US005442067A

United States Patent [19]

Pitteloud

[11] Patent Number: 5,442,067

[45] Date of Patent: Aug. 15, 1995

[54] TETRA-[N-ALKYL-2,2,6,6,-TETRAMETHYL-PIPERIDIN-4-YL]-4,4'-DIPHENYLBISPHOSPHONITE

[75] Inventor: Rita Pitteloud, Praroman, Switzerland

[73] Assignee: Ciba-Geigy Corporation, Ardsley, N.Y.

[21] Appl. No.: 323,478

[22] Filed: Oct. 14, 1994

Related U.S. Application Data

[63] Continuation of Ser. No. 124,130, Sep. 20, 1993, abandoned.

[30] Foreign Application Priority Data

Sep. 25, 1992 [CH] Switzerland ........................ 3008/92

[51] Int. Cl.[6] ........................................ C07F 9/6509

[52] U.S. Cl. ................................ 546/25; 524/102; 523/451; 523/506; 530/213; 106/176; 106/218

[58] Field of Search ...................................... 546/25

[56] References Cited

U.S. PATENT DOCUMENTS

| | | | |
|---|---|---|---|
| 3,825,629 | 7/1974 | Hofer et al. . | |
| 4,096,114 | 6/1978 | Minagawa et al. | 260/45.8 |
| 4,164,494 | 8/1979 | Irick, Jr. | 546/25 |
| 4,325,863 | 4/1982 | Hinsken et al. . | |
| 4,338,244 | 7/1982 | Hinsken et al. . | |

FOREIGN PATENT DOCUMENTS

| | | |
|---|---|---|
| 0281189 | 9/1988 | European Pat. Off. . |
| 2335519 | 7/1977 | France . |
| 290906 | 6/1991 | Germany . |
| 2247241 | 2/1992 | United Kingdom . |

OTHER PUBLICATIONS

U. Hähner, W. D. Habischer and S. Chmbla, *Polym. Degrad. Stab.*, 41 (2) 197–203 (1992).

R. Gächter/H. Müller, Plastics & Additives Handbook 3rd Ed., p. 47 (1990).

W. D. Habicher, et al., J. Prakt. Chemie 334, 333–349 (1992).

C.A. 135099f vol. 87 (1977).

*Primary Examiner*—John C. Bleutge

*Assistant Examiner*—D. R. Wilson

*Attorney, Agent, or Firm*—Luther A. R. Hall; Michele A. Kovaleski

[57] ABSTRACT

Tetra-[N-alkyl-2,2,6,6-tetramethylpiperidin-4-yl]-4,4'-diphenylbisphosphonite Abstract of the Disclosure Novel compounds of formula I (I)

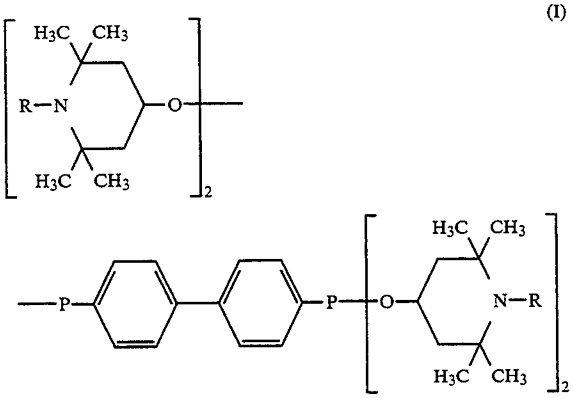

wherein R is $C_1$–$C_4$ alkyl, allyl or benzyl, as stabilisers for protecting organic materials from thermal, oxidative or light-induced degradation.

2 Claims, No Drawings

TETRA-[N-ALKYL-2,2,6,6,-TETRAMETHYL-PIPERIDIN-4-YL]-4,4'-DIPHENYLBISPHOSPHONITE

This is a continuation of application Ser. No. 08/124,130, filed on Sep. 20, 1993, now abandoned.

The present invention relates to novel tetra-[N-alkyl-2,2,6,6-tetramethylpiperidin-4-yl] 4,4'-diphenylbisphosphonites, to compositions comprising an organic material, preferably a polymer, and the novel stabilisers, and to the use thereof for stabilising organic materials against oxidative, thermal or light-induced degradation.

Organic phosphites and phosphonites are known in the art are co-stabilisers, secondary antioxidants and processing stabilisers, inter alia for polyolefins. Typical examples of such known phosphite, phosphonite and bisphosphonite stabilisers will be found in R. Gächter/H. Müller (Ed.), Plastics Additives Handbook, 3rd Ed., p. 47, Hanser, Munich, 1990.

Hindered amines, including in particular compounds containing 2,2,6,6-tetramethylpiperidyl groups, are preferably used as light stabilisers (hindered amine light stabilisers; HALS).

Phosphites or phosphonites containing HALS structural units have been described, inter alia, by W. D. Habicher et al, J. prat. Chem. 33.4, 333-349 (1992) and in GB-A-2 247 241.

There is still a need for effective stabilisers for organic materials that are susceptible to oxidative, thermal and/or light-induced degradation.

It has now been found that a selected group of such bisphosphonites are particularly suitable for use as stabilisers for organic materials that are susceptible to oxidative, thermal and/or light-induced degradation. To be singled out for special mention is the suitability of these compounds as processing stabilisers for synthetic polymers.

Accordingly, the present invention relates to compounds of formula I

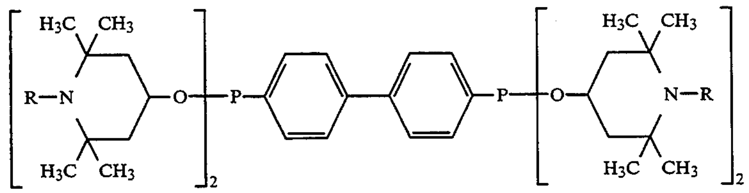

(I)

wherein R is $C_1$–$C_4$ alkyl, allyl or benzyl.

$C_1$–$C_4$ Alkyl denotes an unbranched radical, typically methyl, ethyl, n-propyl or n-butyl. Methyl is preferred.

The compound of formula I, wherein R is methyl or benzyl, is preferred.

The novel compounds of formula I can be prepared in a manner which is known per se.

The preferred procecess typically comprises reacting the 4,4'-diphenyl-(bisdichlorophosphine) of formula II

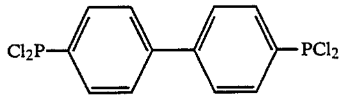

(II)

-continued

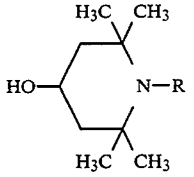

(III)

with at least 4 equivalents of piperidin-4-ol of formula III in the presence of a suitable organic polar or nonpolar aprotic solvent. It is preferred to carry out the reaction in the presence of a base in the temperature range from $-20°$ C. to the boiling point of the solvent. A possible variant of this process comprises using the alcoholate derived from the piperidin-4-ol of formula HI instead of the base.

The base can be used in different amounts, ranging from catalytic through stoichiometric amounts to the multiple molar excess over the piperidin-4-ol of formula III. The hydrogen chloride formed during the reaction is converted by the base into the chloride, which may then be removed by filtration and washing with a suitable aqueous or solid phase. A second, water-immiscible solvent may be used for this purpose. The product is conveniently purified by recrystallising the residue of the organic phase which has been concentrated or evaporated to dryness.

Suitable solvents for carrying out the reaction include hydrocarbons (typically toluene, xylene, hexane, pentane or further petroleum ether fractions), halogenated hydrocarbons e.g. dichloro- or trichloromethane, 1,2-dichloroethane, 1,1,1-trichloroethane), ethers (e.g. diethyl ether, dibutyl ether or tetrahydrofuran), and also acetonitfile, dimethyl formamide, dimethyl sulfoxide, N-methylpyrrolidone.

Suitable base include tertiary mines (e.g. trimethylamine, triethylamine, tributylamine, N,N-dimethylaniline, N,N-diethylaniline, pyridine or the piperidin-4-ol of formula III itself), hydrides (e.g. lithium, sodium or potassium hydride) or alcoholates (e.g. sodium methylate).

Hydrides, alkali metals, alkali metal hydroxides or sodium methylate may also be used for the formation of the alcoholate of piperidin-4-ol of formula 1II. The reaction product (e.g. water, methanol) in this case is distilled off before the reaction with the 4,4'-diphenyl-(bis-dichlorophosphine) of formula II(e.g. as an azeotrope with toluene).

The preparation of the 4,4'-diphenyl-(bisdichlorophosphine) of formula II is disclosed, inter alia, in CH-A-553 827 or DE-A-2 152 481.

The preparation of the piperin-4-ols of formula III is known and disclosed, inter alia, in CH-A-602 644 or CH-A-602 645.

The compounds of formula I have excellent suitability for stabilising organic materials against oxidative, thermal or light-induced degradation. Accordingly, the invention also relates to compositions comprising (a) an organic material susceptible to oxidative, thermal or light-induced degradation and (b) at least one compound of formula I.

Exemplary of such materials are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholams, esters, ethers, amines, alkyls, alkenyls and/or aryls that may be either $\pi$ or $\sigma$-coordinated. These metal complexes may be in the free form or fixed on substrams, typically on activated magnesium chloride, titanium(III) chloride, alumina or silicon oxide. These catalysts may be soluble or insoluble in the polymefisation medium. The catalysts can be used by themselves in the polymerisation or further activators may be used, typically metal alkyls, metal hydrides, metal alkyl halides, metal alkyl oxides or metal alkyloxanes, said metals beeing elements of groups Ia, IIa and/or Ilia of the Periodic Table. The activators may be modified conveniently with further ester, ether, amine or silyl ether groups. These catalyst stystems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic arthydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrerie such as styrene/butadiene/styrene, styrene/isoprene/styrene, styrene/ethylene/butylene/styrene or styrene/ethylene/propylene/styrene.

7. Graft copolymers of styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrerie and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl buryrat, polyallyl phthalate or polyallyl melamine;

as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene aliamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

The invention also relates to compositions comprising as component (a) natural, semi-synthetic or synthetic polymers, preferably thermoplastic polymers, more preferably polyolefins, most preferably polyethylene or polypropylene.

The invention further relates to the use of the compounds of formula I for stabilising organic materials against oxidalive, thermal or light-induced degradation, especially to their use as processing stabilisers (heat stabilisers) for thermoplastic polymers.

The organic materials to be protected are preferably natural, semi-synthetic or, preferably, synthetic organic materials. Thermoplastic polymers are most preferred, especially PVC or polyolefins, most preferably polyethylene and propylene (PP).

The compositions of this invention conveniently contain the compound of formula I in an amount of 0.01 to 10, typically 0.01 to 5, preferably 0.05 to 3 and, most preferably, 0.05 to 1% by weight. The percentages by weight are based on the total amount of said compound. The computation is based on the total weight of the organic material without the compound of formula I.

Incorporation in the organic materials can be effected by blending them with, or by applying thereto, the compound of formula I and further optional additives by methods which are commonly used in the art. If the organic materials are polymers, especially synthetic polymers, the incorporation can be effected before or during the fabrication of shaped articles or by applying the dissolved or dispersed compound to the polymer, with or without subsequent evaporation of the solvent. In the case of elastomers, these may also be stabilised as lattices. A further means of blending the compound of formula I into polymers consists in adding said compound before, during or directly after the polymerisation of the corresponding monomers or before crosslinking. The compound of formula I can also be added in encapsulated form (e.g. in waxes, oils or polymers). If the compound of formula I is added before or during polymerisation, it can also act as regulator for the chain length of the polymers (chain terminator).

The compounds of formula I or mixtures thereof can also be added in the form of a masterbatch which contains these compounds to the polymers to be stabilised, typically in a concentration of 2.5 to 25 % by weight.

The compounds of formula I may conveniently be incorporated by the following techniques:

- as emulsion or dispersion (e.g. to lattices or emulsion polymers),
- as dry mixture while blending additional components or polymer mixtures,
- by direct addition to the processing apparatus (e.g. extruder, internal mixer and the like), and
- as solution or melt.

The stabilised materials can be used in a wide range of forms, typically including sheets, filaments, ribbons, moulded articles, profiles or as binders for paints and varnishes, adhesives or putties.

As already mentioned, the organic materials to be protected are preferably organic, more particularly synthetic polymers. It is especially useful to protect thermoplastic polymers, preferably polyolefins. In this connection, the excellent action of the compounds of formula I as processing stabilisers (heat stabilisers) is to be highlighted. To this end, the compounds of formula I are conveniently added before or during the processing of the polymer. It is, however, also possible to stabilise other polymers (e.g. elastomers) or lubricants and hydraulic fluids against degradation, such as light-induced and/or thermal oxidative degradation. Examples of elastomers will be found among the above list of possible organic materials.

The suitable lubricants and hydraulic fluids may be based on mineral or synthetic oils or mixtures thereof. The lubricants are known to the skilled person and described in the pertinent technical literature, for example in Dieter Klamann, "Schmierstoffe und verwandte Produkte" (Lubricants and Related Products), Verlag Chemie, Weinheim, 1982, in Schewe-Kobek, "Das Schmiermittel-Taschenbuch" (The Lubricant Handbook), Dr. Alfred Hüthig-Verlag, Heidelberg, 1974) and in "Ullmanns Enzykiopädie der technischen Chemie", (Encyclopedia of Industrial Chemistry), Vol. 13, pages 85–94 (Verlag Chemie, Weinheim, 1977).

The invention further relates to a process for protecting organic material against oxidative, thermal and/or light-induced degradation, which comprises incorporating in, or applying to, said material at least one compound of formula I as stabiliser.

In addition to containing the novel compounds, the compositions of the invention, especially if they contain organic, preferably synthetic, polymers, may contain other conventional additives.

Illustrative examples of such further additives are:

1. Antioxidants 1.1. Alkylated rnonophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-do-decylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl) disulfide.

1.5. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol],4,4'-methylenebis(2,6-di-tert-butylphenol), 4,4'-methylenebis(6-tertbutyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenYl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl)-pentane.

1.6.O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)-sulfide, isooctyl-3,5di-tert-butyl-4-hydroxybenzylmercaptoacetate.

1.7. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis-[4-(1,1,3,3-tetramethylbutyl)phenyl]-2,2-bis(3,5-di-tert-butyl-4-hydroxybenzyl)malonate.

1.8. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.9. Triazine Compounds, for example 2,4-bis(octylmercapto)-6-(3,5-di-tert-butyl-4-hydroxyanilinol)-1,3,5-triazine, 2-octylmercapto-4,6-bis(3,5-di-tert-butyl-4- hydroxyanilino)-1,3,5-triazine, 2-octylmercapto-4,6-bis( 3,5-di-tert-butyl-4-hydroxyphenoxy)-1,3,5-triazine, 2,4,6-tris( 3,5-di-tert-butyl-4-hydroxyphenoxy)- 1,2,3-triazine, 1,3,5-tris-(3,5-di-tert-butyl-4-hydroxybenzyl-)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)- 1,3,5-triazine, 1,3,5-tris(3,5-di-tert-butyl-4-hydroxyphenylpropionyl)-hexahydro- 1,3,5-triazine, 1,3,5-tfis(3,5-dicyclohexyl-4-hydroxybenzyl)isocyanurate.

1.10. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzyl-phosphonate, the calcium salt of the monoethyl ester of 3,5-di-tert-butyl-4-hydroxybenzylphosphonic acid.

1.11. Acylaminophenols, for example 4-hydroxylauranilide, 4-hydroxystearanilide, octyl N-(3,5-di-tert-butyl-4-hydroxyphenyl)carbamate.

1.12. Esters of β-(3,5-di-tert-butyl-4-hydroxyphenyl)-ProPionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.13. Esters of β-(5-tert-butyl-4-hydroxy-3-methyl-phenyl)pmpionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydmxyethyl) isocyanurate, N,N'-bis(hydroxyethyl)oxamide, 3-thiaundecanol, 3-thiapentadecanol, trimethylhexanediol, trimethylolpropane, 4-hydroxymethyl- 1-phospha-2,6,7-trioxabicyclo[2.2.2]octane.

1.14 Esters of β-(3,5-dicyclohexyl-4-hydroxyphenyl)-propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl- 1-phospha-2,6,7-trioxabicyclo[2.2.2]octane.

1.15 Esters of 3,5-di-tert-butyl-4-hydroxyphenyl .acetic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl- 1-phospha-2,6,7-trioxabicyclo[2.2.2]octane.

1.16. Amides of β-(3,5-di-tert-butyl-4-hydroxy-phenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)-trimethylenediamine, N,N'-his(3,5-di-tert-butyl-4-hydroxyphenylpropionyl)hydrazine.

2. UV absorbers and light stabilisers 2.1.2-(2'-Hydroxyphenyl)benzotriazoles, for example 2-(2'-hydroxy-5'-methylphenyl)benzotriazole, 2-(3,5'-di-tert-butyl-2'-hydroxyphenyl)benzotriazole, 2-(5'-tert-butyl-2'-hydroxyphenyl)benzotriazole 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl- 2'-hydroxy-5'-methylphenyl)-5-chloro-benzotriazole, 2-(3'-sec-butyl-5'-tert-butyl-2'-hydroxy-phenyl)benzotriazole, 2-(2'-hydroxy-4'-octyloxy-phenyl)benzotriazole, 2-(3',5'-di-tert-amyl-2'-hydroxy-phenyl)benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethyl-hexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)-phenyl)benzotriazole, 2-(3'-tert-butyl-2'-hydroxy-5'-(2-octyloxycarbonylethyl)phenyl)benzotfiazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylene-bis[4-(1,1,3,3-tetramethyl-butyl)-6-benzotriazole-2-ylphenol]; the transesterification product of 2-[3'-tert-butyl-5'-(2-methoxycarbonylethyl)-2'-hydroxyphenyl]2H-benzotriazole with polyethylene glycol 300; [R-$CH_2CH_2$-COO$(CH_2)_3$]$_2$, where R=3'-tert-butyl-4'-hydroxy-5'-2H-benzotriazo! -2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tert-butylbenzoyl) resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butyl-benzylphosphonic acid, nickel complexes of ketoximes, e.g. of 2-hydroxy-4-methylphenyl undecylketoxime, nickel complexes of 1-phenyl-4-1auroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, his(1,2,2,6,6-pentamethylpiperidyl)sebacate, bis(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)-hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl- 1,3,8-triazasprio[4.5]decan-2,4-dion, bis( 1-octyloxy-2,2,6,6-tetramethylpiperidyl)sebacate, bis(1-octyloxy-2,2,6,6-tetramethylpiperidyl)succinate, the condensate of N,N'-bis-(2,2,6,6-tetramethyl-4-piperidyl)hexamethylenediamine and 4-morpholino-2,6-dichloro-l,3,5-triazine, the condensate of 2-chloro-4,6-bis(4-n-butyl-amino-2,2,6,6-tetramethylpiperidyl )- 1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-( 3-aminopropylamino )ethane, 8-acetyl-3-dodecyl-7,7,9,9-tetramethyl-1,3,8-triazaspiro[4.5]decane-2,4-dione, 3-dodecyl- 1-(2,2,6,6-tetramethyl-4-piperidyl)pyrrolidin-2,5-dione, 3-dodecyl-1-( 1,2,2,6,6-pentamethyl-4-piperidyl)pyrrolidine-2,5-dione.

2.7. Oxamides, for example 4,4'-dioctyloxyoxanilide, 2,2'-dioctyloxy-5,5'-di-tert-butoxanilide, 2,2'-didodecyloxy-5,5'-di-tert-butoxanilide, 2-ethoxy-2'-ethoxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and paramethoxy-disubstituted oxanilides and mixtures of o- and p-ethoxy-disubstituted oxanilides.

2.8.2-(2-Hydroxyphenyl)- 1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)- 1,3,5-triazine, 2,4-bis(2-hydroxy-4-propyloxyphenyl)-6-(2,4-dimethylphenyl)-1,3,5-triazine, 2-(2-hydroxy- 4-octyloxyphenyl)-4,6-bis(4-methylphenyl)- 1,3,5-triazine, 2-(2-hydroxy-4-dodecyloxyphenyl)-4,6-bis( 2,4-dimethylphenyl)- 1,3,5-triazine, 2-[2-hydroxy-4-(2hydroxy-3-butyloxy-propoxy)phenyl]-4,6-bis(2,4-dimethyl)- 1,3,5-triazine, 2-[2-hydroxy-4-(2-hydroxy-3-octyloxy-propyloxy)phenyl]-4,6-bis( 2,4-dimethyl)- 1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl-)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaeryt hritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphsophite, tristearyl sorbitol triphosphite, tetrakis(2,4-di-tert-butylphenyl) 4,4'-biphenylene diphosphonite, 6-isooctyl-oxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl)methylphosphite, bis(2,4-di-tert-butyl-6-methylphenyl)ethylphosphite.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, optical brighteners, flameproofing agents, antistatic agents and blowing agents.

11. Benzofuranones and indolinones, for example those disclosed in U.S. Pat. No. 4,325,863 or U.S. Pat. No. 4,338,244, or 3-[4-(2-acetoxyethoxy)phenyl]-5,7-di-tert-butyl-benzofuran-2-one 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)-benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one.

Further preferred compositions comprise, in addition to component (a) and the compounds of formula I, further additives, preferably phenolic antioxidants, light stabilisers or processing stabilisers.

Especially preferred additional additives (stabilisers) are the benzofuran-2-ones disclosed, inter alia, in U.S. Pat. No. 4,325,863 or U.S. Pat. No. 4,338,244.

Typical examples of such benzofuran-2-ones are compounds of formula

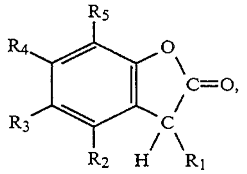

wherein $R_1$ is phenyl or phenyl which is substituted by 1 to 3 alkyl groups together containing not more than 18 carbon atoms, alkoxy of 1 to 12 carbon atoms, alkoxycarbonyl of 2 to 18 carbon atoms or chloro; $R_2$ is-hydrogen;

$R_4$ is hydrogen, alkyl of 1 to 12 carbon atoms, cyclopentyl, cyclohexyl or chloro;

$R_3$ has the significance of $R_2$ or $R_4$ or is a radical of formula $$-(CH_2)_n-\overset{O}{\overset{\|}{C}}-OR_6,\quad -(CH_2)_n-\overset{O}{\overset{\|}{C}}-N(R_7)_2,$$

$$-(CH_2)_n-\overset{O}{\overset{\|}{C}}-O-A-O-\overset{O}{\overset{\|}{C}}-(CH_2)_n-E,$$

$$-(CH_2)_n-\overset{O}{\overset{\|}{C}}-NR_8-A-NR_8-\overset{O}{\overset{\|}{C}}-(CH_2)_n-E,$$

$$-(CH_2)_n-\overset{O}{\overset{\|}{C}}-NR_8-A-O-\overset{O}{\overset{\|}{C}}-(CH_2)_n-E,$$

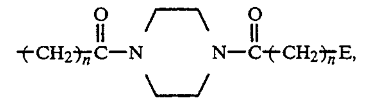

$$-CH_2-S-R_9,\quad -CH(C_6H_5)-\overset{O}{\overset{\|}{C}}-OR_6$$

or —D—E, wherein $R_6$ is hydrogen, alkyl of 1 to 18 carbon atoms, alkyl of 2 to 18 carbon atoms which is interruped by oxygen or sulfur, dialkylarninoalkyl containing altogether 3 to 16 carbon atoms, cyclopentyl, cyclohexyl, phenyl or phenyl which is substituted by 1 to 3 alkyl groups together containing not more than 18 carbon atoms, n is 0, 1 or 2;

the $R_7$ substituents are each independently of the other hydrogen, alkyl of 1 to 18 carbon atoms, cyclopentyl, cyclohexyl, phenyl, phenyl which is substituted by 1 or 2 alkyl groups together containing not more than 16 carbon atoms, a radical of formula $-C_2H_4OH$, $$-C_2H_4-O-C_mH_{2m+1}\quad\text{or}\quad -C_2H_4-O-\overset{O}{\overset{\|}{C}}-R_{10}$$

or, together with the linking nitrogen atom, form a piperidino or morpholino radical;

m is 1 to 18;

$R_{10}$ is hydrogen, alkyl of 1 to 22 carbon atoms or cycloalkyl of 5 to 12 carbon atoms;

A is alkylene of 2 to 22 carbon atoms which may be interrupted by nitrogen, oxygen or sulfur;

$R_8$ is hydrogen, alkyl of 1 to 18 carbon atoms, cyclopentyl, cyclohexyl, phenyl, phenyl which is substituted by 1 or 2 alkyl groups together containing not more than 16 carbon atoms, or benzyl;

$R_9$ is alkyl of 1 to 18 carbon atoms;

D is —O—, —S—, —SO—, $-SO_2$ or $-C(R_{11})_2-$;

the $R_{11}$ substituents are each independently of the other hydrogen, alkyl of not more than 16 carbon atoms, phenyl or a radical of formula $$-(CH_2)_n-\overset{O}{\overset{\|}{C}}-OR_6$$

or $$-(CH_2)_n-\overset{O}{\overset{\|}{C}}-N(R_7)_2,$$

wherein n, $R_6$ and $R_7$ have the given meanings;

E is a radical of formula

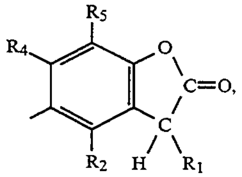

wherein $R_1$, $R_2$ and $R_4$ have the given meanings; and $R_5$ is hydrogen, alkyl of 1 to 20 carbon atoms, cyclopentyl, cyclohexyl, chloro or a radical of formula $$-CH_2-\overset{O}{\overset{\|}{C}}-OR_6\quad\text{or}\quad -CH_2-\overset{O}{\overset{\|}{C}}-N(R_7)_2,$$

wherein $R_6$ and $R_7$ have the given meanings, or $R_5$ together with $R_4$ forms a tetramethylene radical.

Preferred benzofuran-2-ones are those in which $R_3$ is hydrogen, alkyl of 1 to 12 carbon atoms, cyclopentyl, cyclohexyl, chloro or a radical of formula $$-(CH_2)_n-\overset{O}{\overset{\|}{C}}-OR_6,\quad -(CH_2)_n-\overset{O}{\overset{\|}{C}}-N(R_7)_2$$

or —D—E, wherein n, $R_6$, $R_7$, D and E are as defined above, $R_6$ is preferably hydrogen, alkyl of 1 to 18 carbon atoms, cyclopentyl or cyclohexyl.

Further preferred benzofuran-2-ones are those in which $R_1$ is phenyl or phenyl which is substituted by 1 or 2 alkyl groups together containing not more than 12 carbon atoms; $R_2$ is hydrogen; $R_4$ is hydrogen or alkyl of 1 to 12 carbon atoms; $R_3$ is hydrogen, alkyl of 1 to 12 carbon atoms, $$-(CH_2)_n-\overset{O}{\overset{\|}{C}}-OR_6,\quad -(CH_2)_n-\overset{O}{\overset{\|}{C}}-N(R_7)_2$$

or —D—E; $R_5$ is hydrogen, alkyl of 1 to 20 carbon atoms, $$-CH_2-\overset{O}{\overset{\|}{C}}-OR_6\quad\text{or}\quad -CH_2-\overset{O}{\overset{\|}{C}}-N(R_7)_2,$$

or $R_5$ together with $R_4$ forms a tetramethylene radical, in which formulae above n, $R_6$, $R_7$, D and E are as defined at the outset.

Particularly interesting benzofuran-2-ones are also those in which $R_1$ is phenyl; $R_3$ is hydrogen, alkyl of 1 to 12 carbon atoms or —D—E; $R_2$ and $R_4$ are each independently of the other hydrogen or alkyl of 1 to 4 carbon atoms; and $R_5$ is alkyl of 1 to 20 carbon atoms, and D and E are as defined at the outset.

Finally, those benzofuran-2-ones merit particular mention in which $R_1$ is phenyl; $R_3$ is alkyl of 1 to 4 carbon atoms or —D—E; $R_2$ and $R_4$ are hydrogen; and $R_5$ is alkyl of 1 to 4 carbon atoms, cyclopentyl or cyclohexyl, and D is —C($R_{11}$)$_2$— and E is a radical of formula

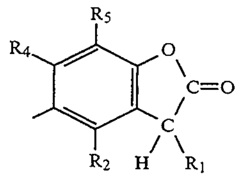

wherein the $R_{11}$ substituents are identical or different and are each alkyl of 1 to 4 carbon atoms, and $R_1$, $R_2$, $R_4$ and $R_5$ have the given meanings.

The amount of further additives, preferably stabilisers, e.g. of the claimed benzofuran-2-ones, can vary over a wide range. The compositions of this invention will typically contain from 0.0005 to 10% by weight, preferably from 0.001 to 5% by weight, most preferaby from 0.01 to 2% by weight, of said additives.

The following Examples illustrate the preparation and use of the novel compound. All percentages are by weight, unless otherwise stated.

Example 1: Preparation of tetra-[1,2,2,6,6-pentamethylpiperidin-4-yl]-4,4'-diphenyl-bisphosphonite.

A solution of 18.0 g (105 mmol) of 1,2,2,6,6-pentamethylpiperidin-4-ol in 125 ml toluene is added dropwise to a solution of 8.90 g (25.0 retool) of 4,4'-diphenyl(bisdichlorophosphine) and 12.15 g (120 retool) of triethylamine in 75 ml of toluene. The reaction mixture is stirred overnight at room temperature, the precipitate is isolated by filtration, and the filtrate is concentrated on a vacuum rotary evaporator, giving 17.6 g (80 %) of tetra-[1,2,2,6,6-pentamethylpiperidin-4-yl]-4,4'-diphenylbisphosphonite.

Analysis (calcd): C 69.77 %; H 9.91%; N 6.26 %; P 6.92 %

Analysis (found): C 69.75 %; H 9.96%; N 6.06 %; P 7.02 %

$^1$H-NMR (300 MHz, $CDCl_3$), δ (H*):

4.26–4.36 ppm (m, 4H, 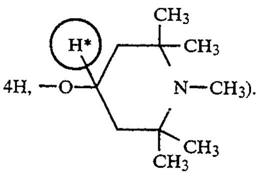

Example 2: Preparation of tetra-[1-benzyl-2,2,6,6-tetramethylpiperidin-4-yl]-4,4'-diphenylbisphosphonite.

A solution of 4.27 g (12.0 mmol) of 4,4'-diphenyl(bisdichlorophosphine) in 20 ml of dichloromethane is added dropwise at c. 10° C. to a solution of 12.17 g (49.0 mmol) of 1-benzyl-2,2,6,6-tetramethylpiperidin-4-ol and 8.4 ml (60.0 retool) of triethylamine in 100 ml of dichloromethane. The reaction mixture is stirred for 30 minutes at room temperature and then refluxed for another 4 hours. The precipitate is isolated by filtration. The flitrate is diluted with c. 50 ml of hexane/toluene=1:1, and the product is filtered once more and concentrated on a vacuum rotary evaporator. Crystallisation of the residue from isopropanol gives 6.3 g (44% ) of tetra-[1-benzyl-2,2,6,6-tetramethylpiperidin-4-yl]-4,4'-diphenylbisphosphonite.

Analysis (calcd): C 76.09%; H 8.74%; N 4.67%; P 5.16%

Analysis (found): C 76.37%; H 9.33%; N 4.80%; P 5.33%

$^1$H-NMR (300 MHz, $CDCl_3$), δ (H*):

3.8 ppm (s, 8H, 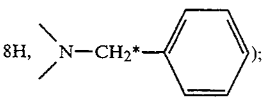);

4.35–4.57 (m, 4H, 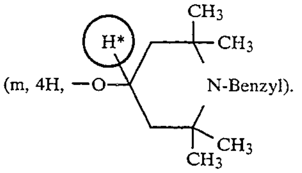

Example 3: Stabilisation of multiple-extruded polypropylene 1.3 kg of polypropylene powder (Profax ®6501 ) which has been prestabilised with 0.025 % of kganox ®1076 (n-octadecyl (3-[3,5-di-tert-butyl-4-hydroxyphenyl]propionate] (having a melt index of 3.2 measured at 230°/216 kg), are blended with 0.05 % of Irganox ® 1010 (pentaerythrityl tetrakis-[3-(3,5-di-tert-butyl-4-hydroxyphenyl)propionate), 0.05 % of calcium stearate, 0.03 % of dihydrotalcite [DHT 4A ®,Kyowa Chemical Industry Co., Ltd., $Mg_{4.5}Al_2(OH)_{13}CO_3.3,5 H_2O$] and 0.05 % of the compound of Example 2. This blend is then extruded at 100 rpm in an extruder having a cylinder diameter of 20 mm and a length of 400 mm, the 3 heating zones being adjusted to the following temperatures: 260° C., 270° C., 280° C. The extrudate is cooled by drawing it through a water bath and then granulated. This granulate is repeatedly extruded. The melt index is measured after 3-extrusions (230° C./2.16 kg/). A substantial increase in the melt index denotes pronounced chain degradation, i.e. poor stabilisation. The results are shown in Table 1.

TABLE 1

| Compound of Example | Melt index after 3 extrusions |
|---|---|
| — | 20.0 |
| Example 2 | 4.7 |

Example 4: Stabilisation of polyethylene during processing 100 parts of polyethylene powder (Lupolen ®5260 Z) are blended with 0.05 part of pentaerythritol tetrakis[3-(3,5-di-tert-butyl-4-hydroxyphenyl)propionate] and 0.01 part of the compound of Example 1 and the blend is kneaded in a Brabender plastograph at 220° C. and 50 rpm. During this time the kneading resistance is recorded continuously as torque. In the course of the kneading time the polymer begins to crosslink after prolonged constancy, as can be determined by the rapid increase in torque. The time taken until a marked increase in torque is shown in Table 2 as a measure of the stabilising action. The longer this time is the better the stabilising action.

TABLE 2

| Compound of Example | Time until increase in torque (min) |
|---|---|
| — | 5.0 |
| Example 1 | 19.5 |

What is claimed is:
1. A compound of formula I
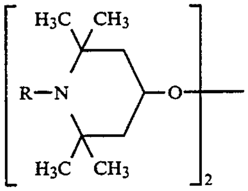
(I)
-continued
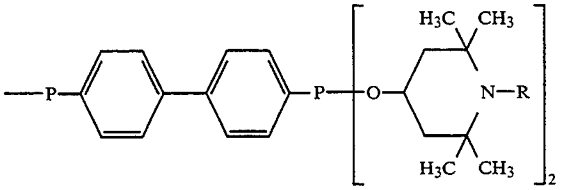
wherein R is $C_1$–$C_4$ alkyl, allyl or benzyl.
2. A compound according to claim 1, wherein R is methyl or benzyl.
* * * * *